(12) United States Patent
Groothuis et al.

(10) Patent No.: US 6,994,718 B2
(45) Date of Patent: Feb. 7, 2006

(54) DISTAL PROTECTION DEVICE FOR FILTERING AND OCCLUSION

(75) Inventors: Adam Groothuis, Lynn, MA (US); Jack Pryor, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 106 days.

(21) Appl. No.: 10/694,944

(22) Filed: Oct. 29, 2003

(65) Prior Publication Data

US 2005/0096691 A1    May 5, 2005

(51) Int. Cl.
A61M 29/00    (2006.01)

(52) U.S. Cl. .................................................. 606/200
(58) Field of Classification Search ........ 606/191–200, 606/213; 604/96.01–109; 128/887; 600/207
See application file for complete search history.

(56) References Cited

U.S. PATENT DOCUMENTS

| | | |
|---|---|---|
| 3,521,620 A | 7/1970 | Cook |
| 3,540,431 A | 11/1970 | Mobin-Uddin |
| 3,952,747 A | 4/1976 | Kimmell, Jr. |
| 3,966,938 A | 6/1976 | Ott et al. |
| 4,080,706 A | 3/1978 | Heilman et al. |
| 4,425,908 A | 1/1984 | Simon |
| 4,456,017 A | 6/1984 | Miles |
| 4,494,531 A | 1/1985 | Gianturco |
| 4,577,631 A | 3/1986 | Kreamer |
| 4,619,246 A | 10/1986 | Molgaard-Nielsen et al. |
| 4,643,184 A | 2/1987 | Mobin-Uddin |
| 4,662,885 A | 5/1987 | DiPisa, Jr. |
| 4,664,113 A | 5/1987 | Frisbie et al. |
| 4,682,599 A | 7/1987 | Konomura |
| 4,688,553 A | 8/1987 | Metals |
| 4,719,924 A | 1/1988 | Crittenden et al. |
| 4,723,549 A * | 2/1988 | Wholey et al. ............. 606/194 |
| 4,723,936 A | 2/1988 | Buchbinder et al. |
| 4,727,873 A | 3/1988 | Mobin-Uddin |
| 4,765,332 A | 8/1988 | Fischell et al. |
| 4,772,258 A | 9/1988 | Marangoni et al. |
| 4,790,812 A | 12/1988 | Hawkins, Jr. et al. |
| 4,793,348 A | 12/1988 | Palmaz |
| 4,794,928 A | 1/1989 | Kletschka |
| 4,817,600 A | 4/1989 | Herms et al. |
| 4,842,579 A | 6/1989 | Shiber |
| 4,848,342 A | 7/1989 | Kaltenbach |
| 4,873,978 A | 10/1989 | Ginsburg |
| 4,921,484 A | 5/1990 | Hillstead |

(Continued)

FOREIGN PATENT DOCUMENTS

DE    3417738 A1    11/1985

(Continued)

OTHER PUBLICATIONS

Palestrant, Aubrey M, et al., *Comparative In Vitro Evaluation of the Nitinol Inferior Vena Cava Filter*, Radiology 145:351-355, Nov. 1982.

Primary Examiner—Anhtuan T. Nguyen
Assistant Examiner—E Houston
(74) Attorney, Agent, or Firm—James F. Crittenden

(57) ABSTRACT

An elongate distal protection device includes an intraluminal filter-occluder combination positioned at a distal end thereof. An expandable occluder is disposed within an expandable filter such that the filter and occluder are independently deployable. During use, the expanded occluder may be used first to stop embolic particles for aspiration thereof. Then, the occluder may be collapsed, leaving the filter expanded to capture any remaining embolic particles.

10 Claims, 10 Drawing Sheets

U.S. PATENT DOCUMENTS

| | | | |
|---|---|---|---|
| 4,926,858 A | | 5/1990 | Gifford, III et al. |
| 4,943,297 A | | 7/1990 | Saveliev et al. |
| 4,957,501 A | | 9/1990 | Lahille et al. |
| 4,990,156 A | | 2/1991 | Lefebvre |
| 5,002,560 A | | 3/1991 | Machold et al. |
| 5,011,488 A | * | 4/1991 | Ginsburg .................... 606/159 |
| 5,041,093 A | | 8/1991 | Chu |
| 5,053,008 A | | 10/1991 | Bajaj |
| 5,071,407 A | | 12/1991 | Termin et al. |
| 5,074,871 A | | 12/1991 | Groshong |
| 5,090,960 A | | 2/1992 | Don Michael |
| 5,092,839 A | | 3/1992 | Kipperman |
| 5,102,415 A | | 4/1992 | Guenther et al. |
| 5,108,418 A | | 4/1992 | Lefebvre |
| 5,108,419 A | | 4/1992 | Reger et al. |
| 5,114,403 A | | 5/1992 | Clarke et al. |
| 5,133,733 A | | 7/1992 | Rasmussen et al. |
| 5,135,487 A | | 8/1992 | Morrill et al. |
| 5,147,379 A | | 9/1992 | Sabbaghian et al. |
| 5,152,777 A | | 10/1992 | Goldberg et al. |
| 5,160,342 A | | 11/1992 | Reger et al. |
| 5,161,427 A | | 11/1992 | Fukuda et al. |
| 5,234,458 A | | 8/1993 | Metais |
| 5,242,462 A | | 9/1993 | El-Nounou et al. |
| 5,300,086 A | | 4/1994 | Gory et al. |
| 5,324,304 A | | 6/1994 | Rasmussen |
| 5,329,942 A | | 7/1994 | Gunther et al. |
| 5,344,427 A | | 9/1994 | Cottenceau et al. |
| 5,350,398 A | | 9/1994 | Pavcnik et al. |
| 5,358,486 A | | 10/1994 | Saab |
| 5,370,657 A | | 12/1994 | Irie |
| 5,375,612 A | | 12/1994 | Cottenceau et al. |
| 5,376,094 A | | 12/1994 | Kline |
| 5,383,887 A | | 1/1995 | Nadal |
| 5,397,305 A | | 3/1995 | Kawula et al. |
| 5,397,306 A | | 3/1995 | Nobuyoshi et al. |
| 5,413,586 A | | 5/1995 | Dibie et al. |
| 5,415,630 A | | 5/1995 | Gory et al. |
| 5,421,832 A | | 6/1995 | Lefebvre |
| 5,480,382 A | | 1/1996 | Hammerslag et al. |
| 5,484,424 A | | 1/1996 | Cottenceau et al. |
| 5,531,788 A | | 7/1996 | Dibie et al. |
| 5,549,626 A | | 8/1996 | Miller et al. |
| 5,601,595 A | | 2/1997 | Smith |
| 5,626,605 A | | 5/1997 | Irie et al. |
| 5,649,953 A | | 7/1997 | Lefebvre |
| 5,681,347 A | | 10/1997 | Cathcart et al. |
| 5,683,411 A | | 11/1997 | Kavteladze et al. |
| 5,695,518 A | | 12/1997 | Laerum |
| 5,695,519 A | | 12/1997 | Summers et al. |
| 5,720,764 A | | 2/1998 | Naderlinger |
| 5,725,550 A | | 3/1998 | Nadal |
| 5,746,758 A | | 5/1998 | Nordgren et al. |
| 5,746,767 A | | 5/1998 | Smith |
| 5,755,790 A | | 5/1998 | Chevillon et al. |
| 5,769,816 A | * | 6/1998 | Barbut et al. ............ 604/93.01 |
| 5,795,322 A | | 8/1998 | Boudewijn |
| 5,800,391 A | | 9/1998 | Kontos |
| 5,800,457 A | | 9/1998 | Gelbfish |
| 5,800,525 A | | 9/1998 | Bachinski et al. |
| 5,810,874 A | | 9/1998 | Lefebvre |
| 5,814,064 A | | 9/1998 | Daniel et al. |
| 5,827,324 A | | 10/1998 | Cassell et al. |
| 5,836,968 A | | 11/1998 | Simon et al. |
| 5,836,969 A | | 11/1998 | Kim et al. |
| 5,846,260 A | | 12/1998 | Maahs |
| 5,853,420 A | | 12/1998 | Chevillon et al. |
| 5,865,800 A | | 2/1999 | Mirarchi et al. |
| 5,876,367 A | | 3/1999 | Kaganov et al. |
| 5,911,734 A | | 6/1999 | Tsugita et al. |
| 5,935,139 A | | 8/1999 | Bates |
| 5,972,019 A | | 10/1999 | Engelson et al. |
| 6,051,014 A | | 4/2000 | Jang |
| 6,066,158 A | * | 5/2000 | Engelson et al. ........... 606/200 |
| 6,090,097 A | | 7/2000 | Barbut et al. |
| 6,123,715 A | | 9/2000 | Amplatz |
| 6,165,200 A | | 12/2000 | Tsugita et al. |
| 6,171,327 B1 | | 1/2001 | Daniel et al. |
| 6,179,859 B1 | | 1/2001 | Bates et al. |
| 6,203,552 B1 | | 3/2001 | Bagley et al. |
| 6,235,044 B1 | | 5/2001 | Root et al. |
| 6,258,115 B1 | | 7/2001 | Dubrul |
| 6,264,672 B1 | | 7/2001 | Fisher |
| 6,277,138 B1 | | 8/2001 | Levinson et al. |
| 6,277,139 B1 | | 8/2001 | Levinson et al. |
| 6,325,815 B1 | | 12/2001 | Kusleika et al. |
| 6,325,822 B1 | | 12/2001 | Chouinard et al. |
| 6,336,934 B1 | | 1/2002 | Gilson et al. |
| 6,346,116 B1 | | 2/2002 | Brooks et al. |
| 6,364,895 B1 | | 4/2002 | Greenhalgh |
| 6,368,339 B1 | | 4/2002 | Amplatz |
| 6,375,670 B1 | | 4/2002 | Greenhalgh |
| 6,395,014 B1 | | 5/2002 | Macoviak et al. |
| 6,398,773 B1 | | 6/2002 | Bagaoisan et al. |
| 6,406,471 B1 | | 6/2002 | Jang et al. |
| 6,432,122 B1 | | 8/2002 | Gilson et al. |

FOREIGN PATENT DOCUMENTS

| | | |
|---|---|---|
| DE | 3900517 A1 | 7/1989 |
| DE | 4030998 C2 | 4/1991 |
| FR | 2580504 | 10/1986 |
| WO | WO 92/03097 | 3/1992 |
| WO | WO 93/12723 | 7/1993 |
| WO | WO 94/12136 | 6/1994 |
| WO | WO 96/01591 | 1/1996 |
| WO | WO 99/22673 | 5/1999 |

* cited by examiner

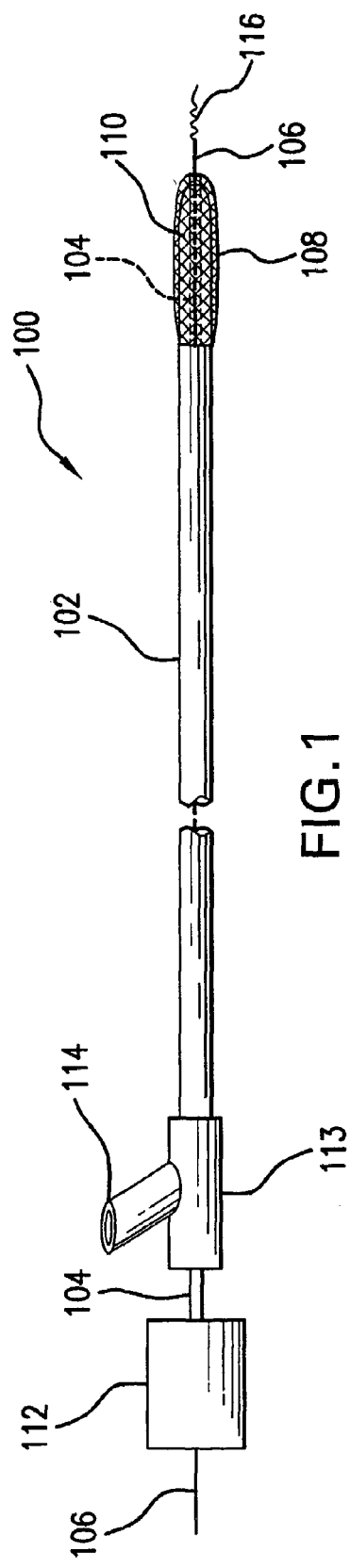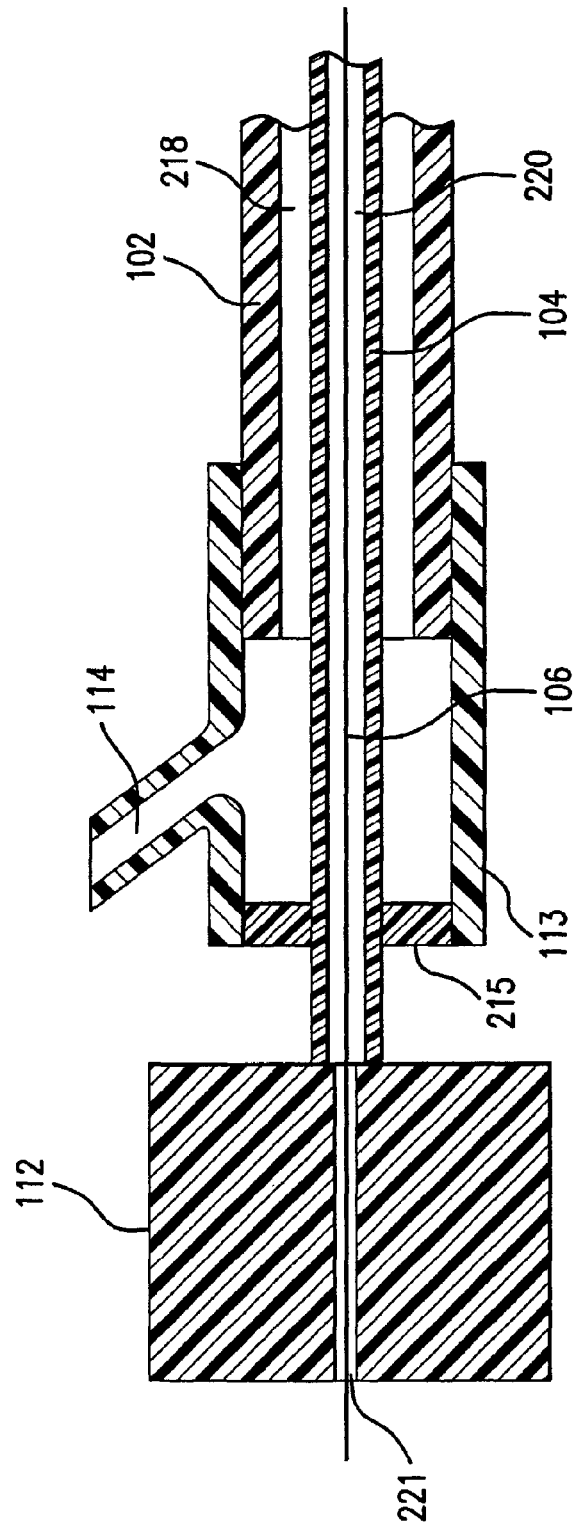

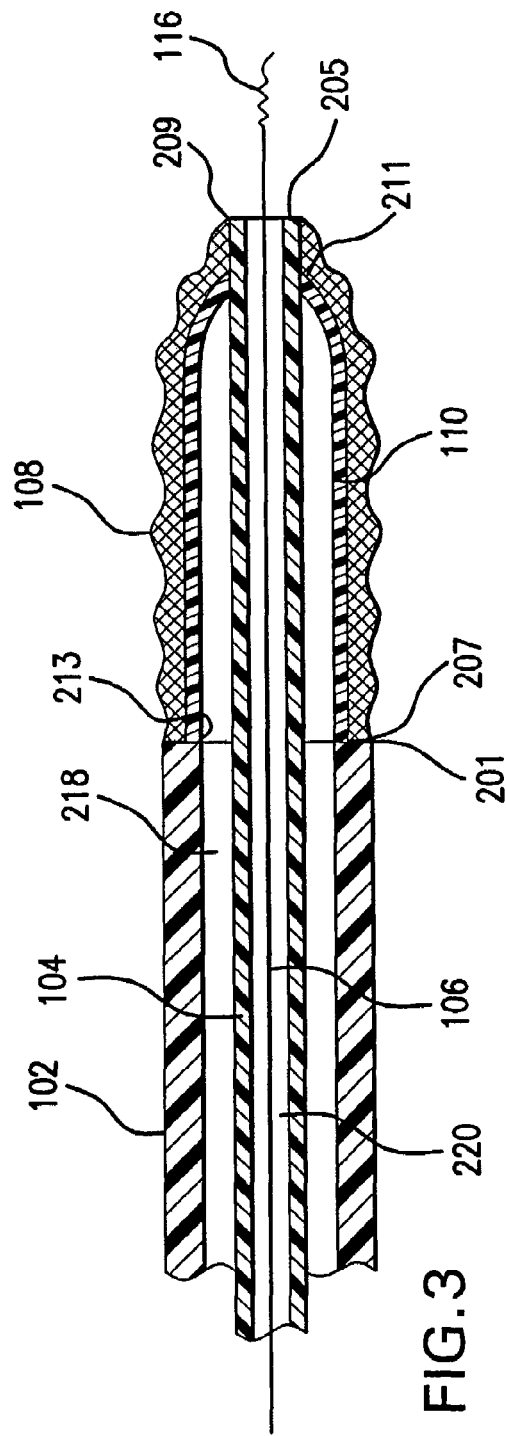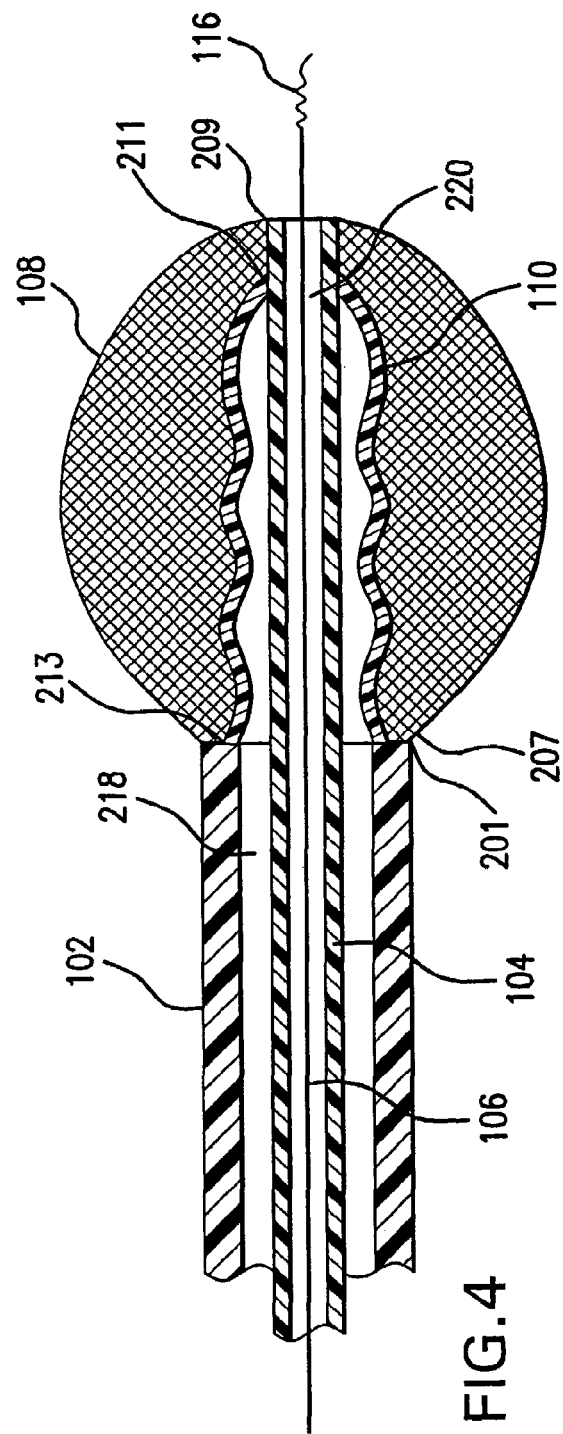

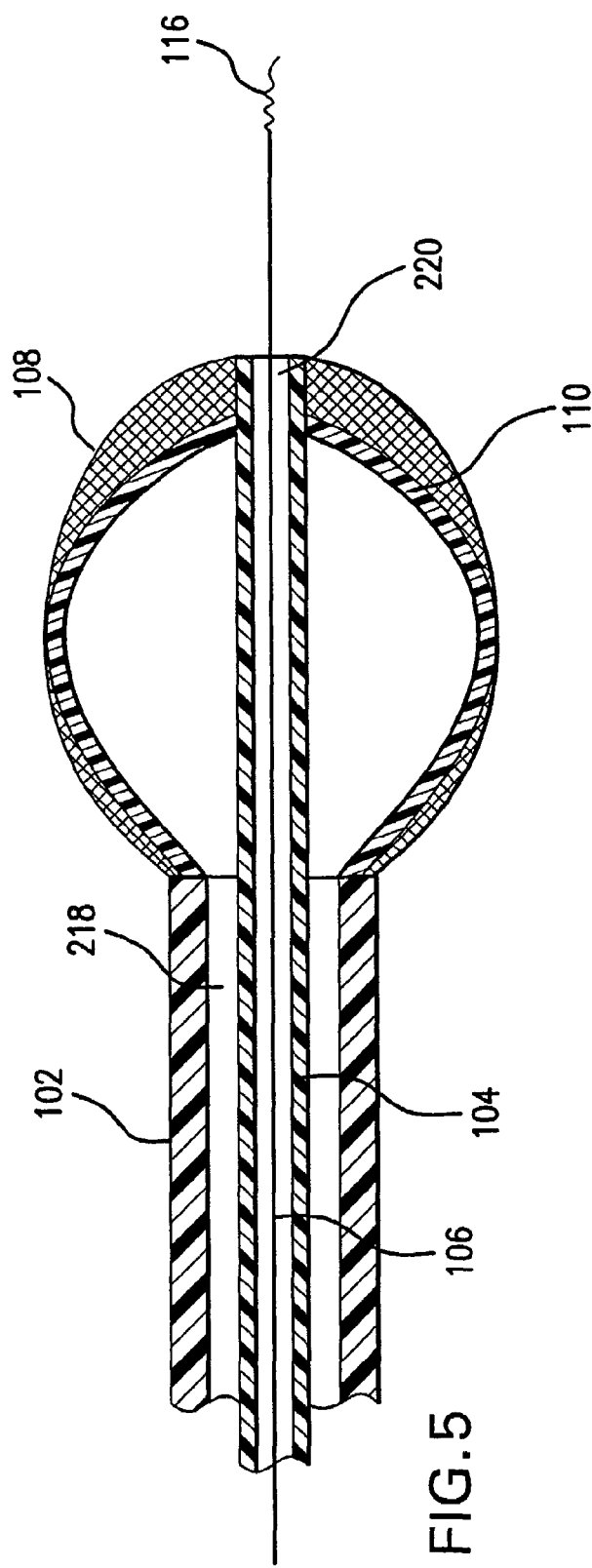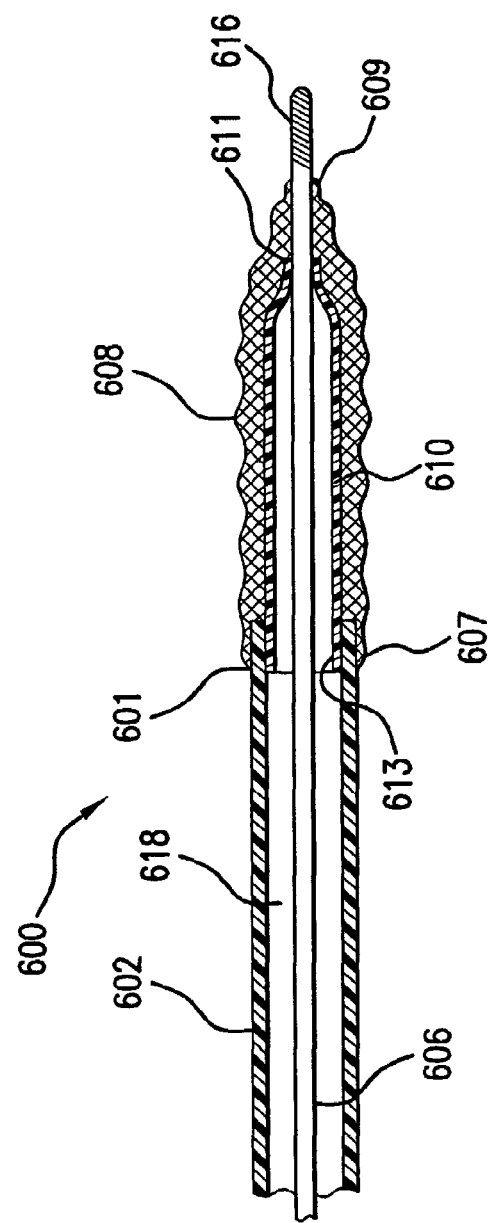

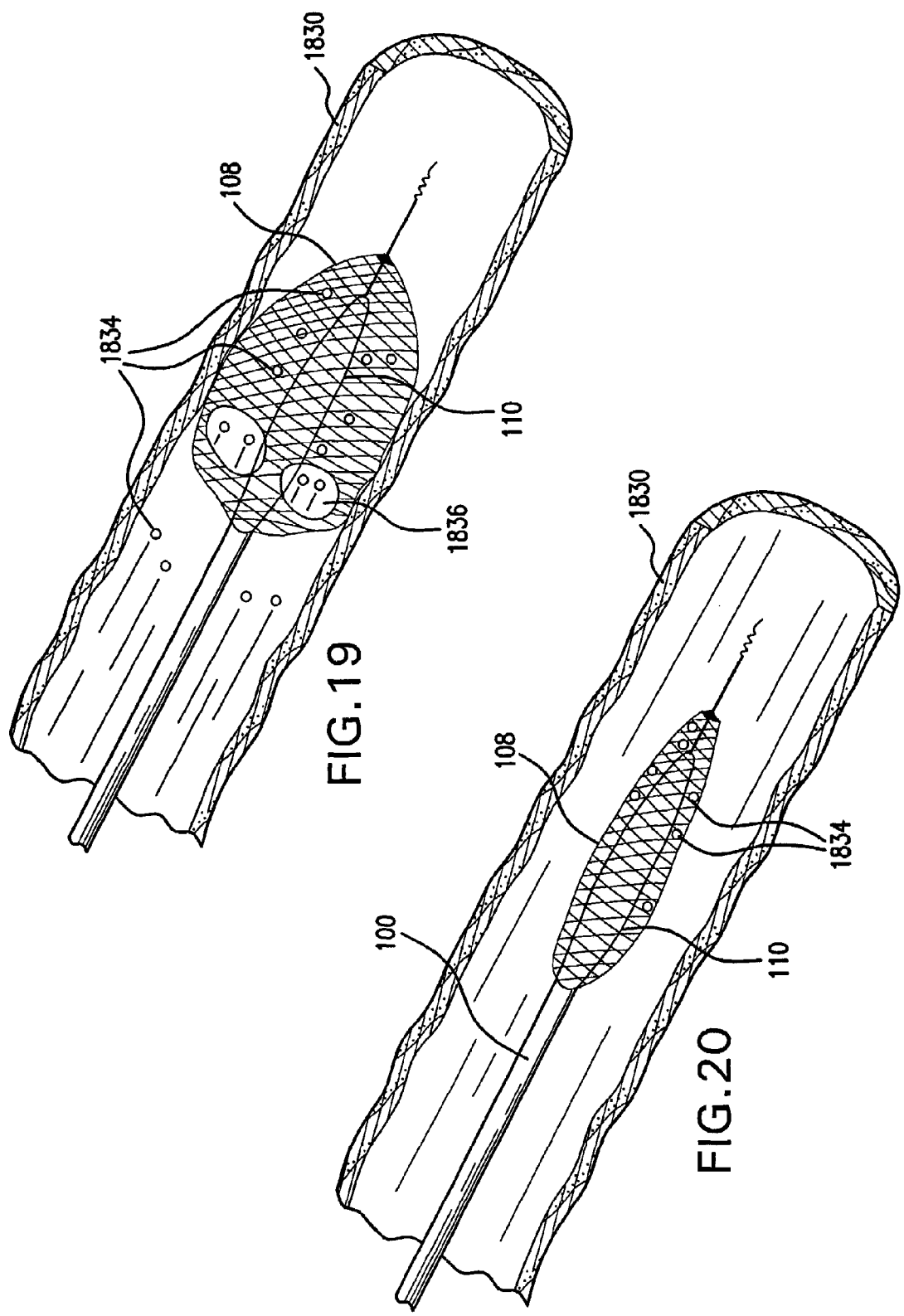

DISTAL PROTECTION DEVICE FOR FILTERING AND OCCLUSION

BACKGROUND OF THE INVENTION

1. Field of the Invention

The present invention relates to catheter distal protection devices, and specifically to filter and occluder mechanisms for use during intravascular procedures to capture embolic particles.

2. Background of the Invention

Diseased blood vessels are a widespread medical condition. For example, a narrowing, or stenosis may form by local thickening of the vessel walls, or a lesion may form by an accumulation of atherosclerotic plaque on blood vessel walls. A thrombus (blood clot) may also form in a vessel, especially in a region of turbulent flow adjacent a narrowing. Blood vessel walls may also become thin and weak, possibly leading to the formation of an aneurysm. If a blood vessel becomes weakened or narrowed, clinical intervention may be required to prevent rupture or complete occlusion of the vessels. While many different surgical procedures are associated with the treatment of vascular diseases, the use of catheters is generally preferred due to the minimally invasive nature of interventional catheterization.

Many types of procedures involve the use of catheters to treat stenotic vessels or thromboses. One type of procedure is percutaneous transluminal coronary angioplasty, or PTCA, which involves the inflation of a balloon within a stenosis to expand a coronary blood vessel. Additionally, a stent may be implanted in conjunction with PTCA to support the dilated artery. Various other procedures are also common, such as a thrombectomy to remove a thrombus or a portion thereof, or an atherectomy to cut or abrade a stenosis within a diseased portion of the vessel.

Each of these intravascular procedures is associated with a common risk: that an embolic particle may be dislodged during the procedure and migrate through the circulatory system, possibly causing ischaemia, infarctions or strokes. To prevent damage caused by such loosened debris, practitioners may attempt to capture the embolic particles using temporary distal protection devices such as occluder catheters or filter guidewires. Particles that are trapped or collected by such devices may be aspirated from the body lumen, chemically lysed in situ, or removed with the distal protection device at the end of the procedure.

Known distal protection devices have relative advantages and drawbacks. Occlusion devices can prevent all of the embolic debris from migrating such that the stopped debris may then be removed by an aspiration mechanism. However, the duration of use of an occluder is limited because an occluder also blocks blood flow. Therefore, occlusion is not appropriate in all cases. Further, aspirating the stopped embolic particles can be an imperfect process, and some embolic particles may escape when the occluder is collapsed for withdrawal.

Embolic filters also suffer from some drawbacks. Embolic filters may be used for longer duration than occluders because filtering devices do not prevent the flow of fluid. However, embolic filters may be limited in their ability to remove very small embolic particles from the bloodstream. Further, embolic filters may become full of embolic debris and occlude the vessel unless they are emptied by aspiration or removed from the patient's vessel.

Therefore, a need exists in the art to obtain the benefits associated with occluders, such as complete particle capture, while also being able to re-capture particles that may be lost during the collapse of an occluder if aspiration was imperfect. An embolic filter and occluder combination may fill such a need.

A combination of filters and occluders on the same catheter has been proposed for use in heart surgery where the heart must be arrested and isolated from the rest of the cardiovascular system. For example, U.S. Pat. No. 6,090,097 to Barbut et al., the entirety of which is incorporated herein by reference thereto, discloses a balloon arterial cannula that includes a balloon occluder and a blood filtration assembly. However, in this device, the filter and occluder are spatially separated along the shaft of the cannula. Such a separation distance is not practical for use in, for example, an angioplasty procedure.

Further, medical balloons are often used to deploy implantable filters, such as vena cava filters. Such a filter is described in U.S. Pat. No. 4,793,348 to Palmaz, the entirety of which is incorporated herein by reference thereto. This type of filter is detached from the catheter and is permanently implanted to provide prophylaxis in case a blood clot moves into the major veins. Also, balloons used for the deployment of this type of filter are not intended to occlude the vessel for the capture of embolic particles.

Therefore, a need exists in the art for an embolic filter-occluder combination for use as a distal protection device during the treatment of diseased vessels.

SUMMARY OF THE INVENTION

The instant invention provides a temporary distal protection catheter having a filter-occluder combination. An expandable occluder is disposed within an expandable filter at the distal end of the catheter. In an embodiment, the filter is mechanically deployed by relative longitudinal movement of the elongate elements to which it is mounted. In another embodiment, the filter is deployed by the expansion of a balloon. In an embodiment, the occluder may be expanded by a push-pull mechanism similar to that of the filter. In another embodiment, the occluder may be expanded by hydraulic inflation. In an embodiment of the present invention, the filter may be operated (i.e., expanded or collapsed) independently of the occluder. Thus, the occluder may be used first to efficiently capture embolic particles. After aspiration of these captured particles, the occluder may be collapsed, leaving the filter expanded to re-capture any remaining particles.

BRIEF DESCRIPTION OF THE DRAWINGS/FIGURES

Features, aspects and advantages of the present invention will become better understood with reference to the following description, appended claims, and accompanying drawings wherein:

FIG. 1 illustrates a side view of a distal protection system according to the present invention.

FIG. 2 illustrates a longitudinal cross-sectional view of a proximal end of the distal protection system of FIG. 1.

FIG. 3 illustrates a longitudinal cross-sectional view of a distal end of the distal protection system of FIG. 1, shown in a fully collapsed configuration.

FIG. 4 illustrates a longitudinal cross-sectional view of the distal end of the distal protection system of FIG. 1, shown with the filter expanded.

FIG. 5 illustrates a longitudinal cross-sectional view of the distal end of the distal protection system of FIG. 1, shown with both the filter and the occluder expanded.

FIG. 6 illustrates a longitudinal cross-sectional view of a distal end of a second embodiment of the distal protection system according to the present invention, shown in a fully collapsed configuration.

FIG. 19 is a cut-away perspective view of the distal protection system of FIG. 1, shown with the filter expanded in a body lumen.

FIG. 20 is a cut-away perspective view of the distal protection system of FIG. 1, shown in a fully collapsed configuration in a body lumen.

Figure 7:
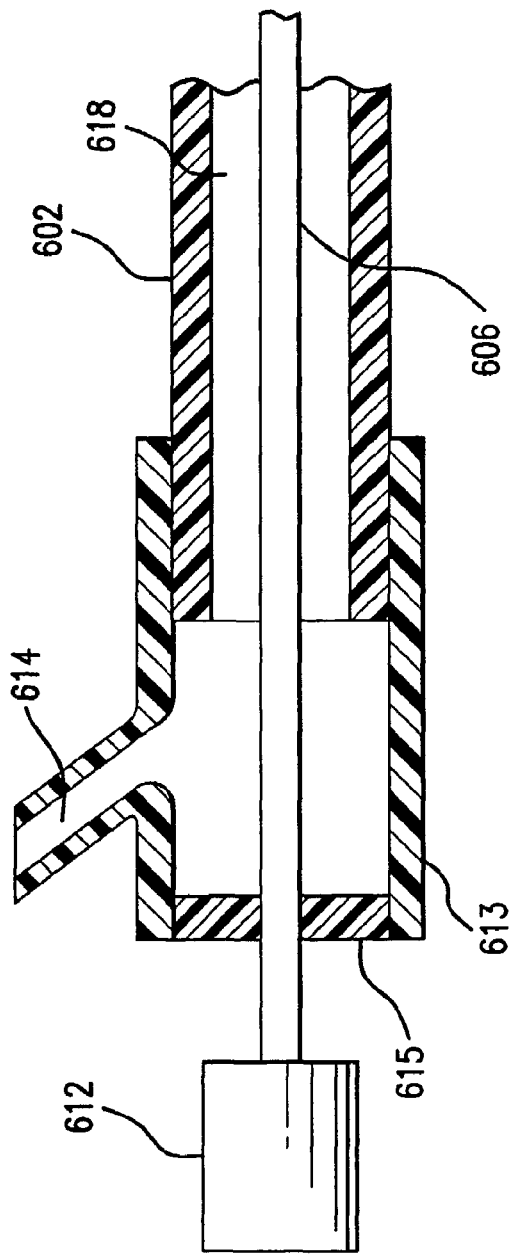
FIG. 7 illustrates a longitudinal cross-sectional view of a proximal end of the distal protection system of FIG. 6.

The drawings are not to scale.

DETAILED DESCRIPTION OF THE INVENTION

Specific embodiments of the present invention are now described with reference to the figures, wherein like reference numbers indicate identical or functionally similar elements. The various disclosed embodiments of the inventive distal protection device are intended for use in conjunction with interventional catheters during therapeutic procedures, examples of such procedures have been described above. Distal protection devices may be catheters that can extend alongside and distally beyond the therapeutic catheter that is being used to treat a diseased region of a body vessel. Alternatively, the distal protection device may be a guidewire that is extendable through a lumen of the therapeutic catheter. Distal protection devices of the guidewire type may be steered and/or advanced through the patient's vasculature before, during, or after the catheter has been positioned for the intended treatment. The disclosed embodiments are described in the context of vascular interventions. However, it should be understood that the invention is equally applicable to the treatment of other vessels within the human body.

FIG. 1 illustrates a distal protection system 100, including an outer tube 102 having a first lumen 218 (shown in FIG. 2), an inner tube or a hollow push rod 104 having a second lumen 220 (shown in FIG. 2), and an inner wire 106. Inner wire 106 is an elongate flexible wire similar to guidewires or corewires known for use with medical catheters. Any materials, dimensions and construction appropriate for use in medical guidewires or corewires are suitable for inner wire 106, depending upon the type of procedure for which distal protection system 100 is intended. As a non-limiting example only, for use in a PTCA procedure, the length of inner wire 106 may be approximately 175 cm, and the diameter of inner wire 106 may be in the range of 0.012" to 0.018". The distal end of inner wire 106 may include a flexible tip 116, which can be a coil spring or other flexible tubular member, as known to those of skill in the art of medical guidewires.

As illustrated in FIGS. 2–5, inner wire 106 is slidably disposed within and extends through second lumen 220 of hollow push rod 104. Distal protection system 100 may be termed an "over-the-wire" configuration because inner wire 106 is slidable within, and removable from this embodiment. Hollow push rod 104 is an elongate, hollow tube having flexibility for navigating tortuous pathways of the cardiovascular system, and having sufficient axial stiffness to deploy distal elements, as will be described in detail below. Hollow push rod 104 may be made as a tube of metal or plastic, or a combination of these materials. Suitable polymeric materials include PEBAX® and similar polyethylene block amide copolymers, polyvinyl chloride, polyethylene, polyethylene terephthalate, polyamide, polyimide, and blends or multi-layered combinations of the same. Further, an optional layer of a stiff reinforcing material may be incorporated to enhance the pushability of push rod 104 and/or distal protection system 100. The reinforcing material may be embedded within the main material of hollow push rod 104 for a portion or the entirety thereof. For example, a braid of metal or polymeric filaments could be included. If made from a polymer, hollow push rod 104 can be manufactured by any method known in the art, such as by extrusion. Thin-walled hypotubing, made of metals such as stainless steel or nitinol, may be used to form all or portions of hollow push rod 104.

FIG. 2 illustrates a proximal end of distal protection system 100, wherein a fitting 113 is sealingly affixed to a proximal end of outer tube 102. Fitting 113 includes an inflation port 114, which is in fluid communication with first lumen 218 within outer tube 102. Inflation port 114 is adapted to be removably attachable to a source of inflation fluid, such as a syringe (not shown). Fitting 113 also includes a proximal gasket 215, which provides a sliding seal around hollow push rod 104. Gasket 215 may be a fixed type or a manually adjustable, Touhy-Borst adapter (not shown).

As shown in FIGS. 2 and 3, a distal end of inner wire 106 extends beyond the push rod's distal end 205 and a proximal end of inner wire 106 extends proximally from a handle 112, which is mounted at a proximal end of push rod 104. In the embodiment shown in FIG. 2, an opening 221 extends through handle 112. Inner wire 106 may be drawn proximally through opening 221 and, if desired, removed from system 100. For the purposes of example only, in a PTCA procedure wherein inner wire 106 has a length of 175 cm, the length of hollow push rod 104 can be approximately 150 cm.

FIG. 3 shows hollow push rod 104 being slidably disposed through first lumen 218 within outer tube 102. Outer tube 102 may incorporate materials and construction similar to those described above regarding hollow push rod 104 and the dimensions for outer tube 102 may vary depending upon the intended use of distal protection system 100. For the purposes of example only, in a typical PTCA procedure, a therapeutic catheter is approximately 135 cm in length. For use with this procedure, outer tube 102 would be at least 140 cm in length, so that it may extend distally beyond the therapeutic catheter to trap any dislodged embolic particles in the antegrade flow of blood.

The inner and outer diameters of hollow push rod 104 and outer tube 102 will vary depending upon the intended use of distal protection system 100. First lumen 218 is used for passage of inflation fluid to and from an occluder 110, as will be described below. Therefore, the outer diameter of hollow push rod 104 should be smaller than the inner diameter of outer tube 104 by an amount sufficient to define an adequate annular flow path within first lumen 218.

FIG. 3 shows a filter 108 within occluder 110, which are disposed about a distal region of hollow push rod 104, i.e., the region that extends beyond outer tube 102. Filter 108 may be any type of expandable filter known in the art. In one embodiment, filter 108 is a tubular mesh of braided filaments with most of the pores having a first pore size for capturing embolic particles. In an embodiment of the present invention, at least one of the pores on a proximal end 207 of filter 108 is significantly larger than the other pores to provide an inlet for the flow of blood and embolic particles into filter 108. In another embodiment, filter 108 comprises a series of filaments or other support struts with a porous membrane mounted over a distal portion thereof, thus forming an umbrella-shaped filter element for capturing embolic debris.

The filaments used for filter 108 may be made from any suitable biocompatible material. Such materials may include metals, such as stainless steels, cobalt alloys and nitinol, or various plastics. Braiding filaments having enhanced radiopacity may also be used to facilitate fluoroscopic visualization of filter 108 within the patient. Radiopacity may be enhanced by making or coating the filaments with a biocompatible metal having a relatively high X-ray attenuation coefficient. Examples of such metals include gold, platinum, tungsten, or alloys thereof. Also, drawn-filled tubing (DFT) wires may be used, wherein either an outer case or an inner core of the DFT wire is made from a radiopaque material.

FIG. 3 shows occluder 110 within filter 108, which are disposed about a distal region of hollow push rod 104, i.e., the region that extends beyond outer tube 102. Filter 108 may be any type of expandable filter known in the art. In one embodiment, filter 108 is a tubular mesh of braided filaments with most of the pores having a first pore size for capturing embolic particles. In an embodiment of the present invention, at least one of the pores on a proximal end 207 of filter 108 is significantly larger than the other pores to provide an inlet for the flow of blood and embolic particles into filter 108. In another embodiment, filter 108 comprises a series of filaments or other support struts with a porous membrane mounted over a distal portion thereof, thus forming an umbrella-shaped filter element for capturing embolic debris.

FIG. 4 illustrates filter 108 having been expanded for apposition against a body vessel wall (not shown) by moving filter proximal and distal ends 207, 209 towards each other. Outer tube 102 and hollow push rod 104 control relative displacement of the ends of filter 108, causing transformation of filter 108 between a collapsed configuration, as shown in FIG. 3, and a deployed configuration, as shown in FIG. 4. In the deployed configuration, hollow push rod 104 has been pulled proximally and/or outer tube 104 has been pushed distally.

Referring again to FIG. 3, inflatable occluder 110 is disposed within filter 108. This nested arrangement is axially compact and minimizes the overall length of the combined distal protection elements. Since distal protection elements are normally positioned downstream of the treatment location, this relatively short arrangement of two distal protection elements allows treatment of stenoses that are located more distally in the patient's vasculature.

Inflatable occluder 110 may be any type of medical balloon known in the art, such as an inelastic balloon with a working length, a working diameter, and tapered ends. Preferably, occluder 110 is an elastic balloon that can deflate and/or stretch longitudinally inside filter 108 without the attendant bulkiness caused by folding or wrinkling. Some examples of materials used for medical balloons known in the art include inelastic polymers, such as polyethylene, polyvinylchloride, and polyethylene terephthalate, and elastic materials, such as silicone, latex, PEBAX® and similar polyethylene block amide copolymers, PELLETHANE® and similar thermoplastic polyurethane elastomers, C-FLEX® and similar styrene-ethylene-butadiene-styrene.

An occluder distal end 211 is fixedly and sealingly attached adjacent push rod distal end 205. An occluder proximal end 213 is fixedly and sealingly attached to outer tube distal end 201, thus placing an interior of occluder 110 in fluid communication with first lumen 218. A proximal occluder joint at outer tube distal end 201 can be located on the inner or outer surface of outer tube 102, and a joint area of outer tube 102 can be tapered or stepped to provide a lower attachment profile. Alternatively, occluder proximal end 213 can be mounted between filter proximal end 207 and outer tube distal end 201. Occluder 110 may be inflated into the deployed or expanded configuration, as shown in FIG. 5, by injection of inflation fluid, such as dilute radiopaque contrast, into proximal inflation port 114 (shown in FIGS. 1 and 2), through first lumen 218, and into occluder 110.

Although filter 108 and occluder 110 are nested, each of these expandable protection elements has a separate deployment mechanism. For example, filter 108 may be deployed by relative displacement of outer tube 102 and hollow push rod 104 while occluder 110 remains uninflated. Then, occluder 110 can be inflated, if desired, within expanded filter 108. Alternatively, filter 108 and occluder 110 can be expanded simultaneously by inflating occluder 110 while outer tube 102 and hollow push rod 104 are permitted to slide with respect to each other. After both expandable elements have been deployed, occluder 110 can be deflated while filter 108 remains expanded. Filter 108 and occluder 110 can also be collapsed together by simultaneously operating both deployment mechanisms, or by manipulating outer tube 102 and hollow push rod 104 while port 114 is left open to vent inflation fluid from occluder 110.

FIG. 6 illustrates a second embodiment of the invention. A distal protection device 600 includes an outer tube 602 having a first lumen 618 therethrough, and an inner wire 606, which is slidably disposed through first lumen 618 and is similar to inner wire 106, described above. A distal flexible tip 616, similar to distal flexible tip 116, may also be included. Distal protection system 600 may be termed a "fixed-wire" embodiment because inner wire 606 is slidable within, but not removable from, first lumen 618. This fixed-wire embodiment of distal protection system 600 eliminates hollow push rod 104 of distal protection system 100, thus permitting outer tube 602 to have a smaller outer diameter, which would be desirable, for example, to fit the device within the guidewire lumen of a therapeutic catheter.

FIG. 7 illustrates a proximal end of distal protection system 600, wherein a fitting 613 is sealingly affixed to a proximal end of outer tube 602 and a handle 612 is fixedly attached to a proximal end of inner wire 606. Fitting 613 includes an inflation port 614, which is in fluid communication with first lumen 618 within outer tube 602. Inflation port 614 is adapted to be removably attachable to a source of inflation fluid, such as a syringe (not shown). Fitting 613 also includes a proximal gasket 615, which provides a sliding seal around inner wire 606. Gasket 615 may be a fixed-type or a manually adjustable, Touhy-Borst adapter (not shown).

Figure 8:
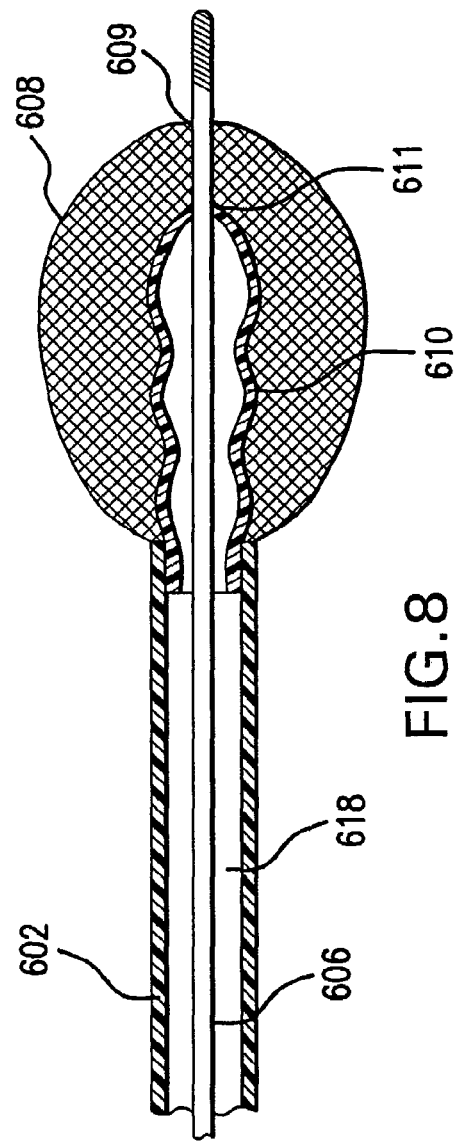
FIG. 8 illustrates a longitudinal cross-sectional view of the distal end of the distal protection system of FIG. 6, shown with the filter expanded.

Filter 608 may be any filter known in the art, as described above with respect to filter 108. As shown in FIG. 6, a filter distal end 609 is fixedly attached to inner wire 606 adjacent flexible tip 616. A filter proximal end 607 is fixedly attached to an outer tube distal end 601. As described above regarding distal protection system 100, the proximal filter attachment at outer tube distal end 601 can be located on an inner or outer surface of outer tube 602, which can also be tapered or stepped in diameter to provide a lower joint profile. When outer tube 602 is pushed distally and/or inner wire 606 is pulled proximally, filter 608 expands to the deployed configuration shown in FIG. 8. As hollow outer tube 602 is pulled proximally and/or inner wire 606 is pushed distally, filter 608 collapses to the original collapsed configuration shown in FIG. 6.

Figure 9:
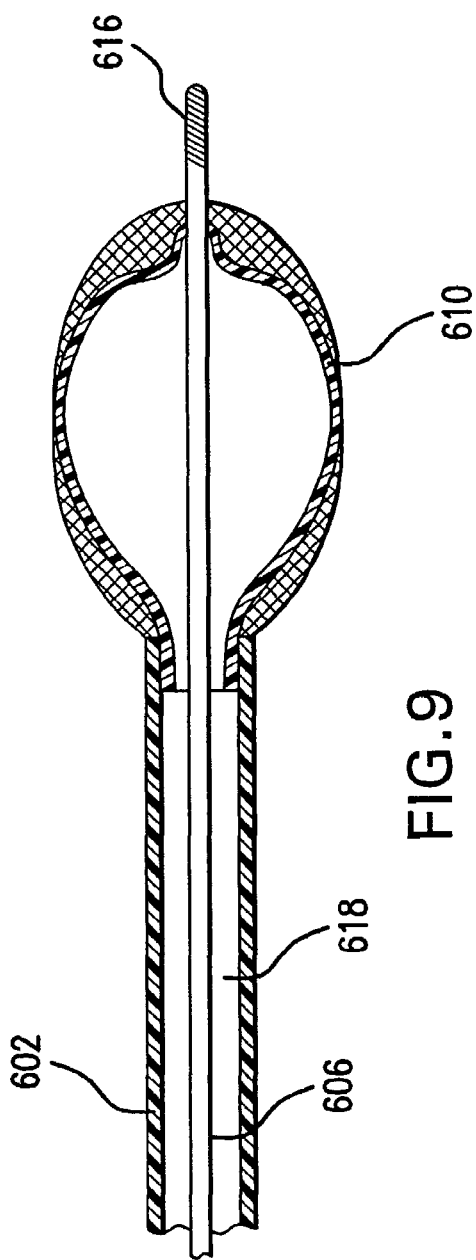
FIG. 9 illustrates a longitudinal cross-sectional view of the distal end of the distal protection system of FIG. 6, shown with both the filter and the occluder expanded.

Referring again to FIG. 6, an inflatable occluder 610, such as a medical balloon, is disposed within filter 608. Like the embodiment of distal protection system 100, this nested arrangement is axially compact and minimizes the overall length of the combined distal protection elements. Similar to occluder 110, described above, inflatable occluder 610 may be any type of medical balloon known in the art. In this embodiment, an occluder proximal end 613 is fixedly and sealingly attached to outer tube distal end 601, placing an interior of occluder 610 in fluid communication with first lumen 618. The proximal occluder joint at outer tube distal end 601 can be located on the inner or outer surface of outer tube 602, and the joint area of outer tube 602 can be tapered or stepped to provide a lower attachment profile. Alternatively, occluder proximal end 613 can be mounted between filter proximal end 607 and outer tube distal end 601. An occluder distal end 611 is fixedly and sealingly attached to inner wire 606. Occluder 610 may be inflated into the deployed or expanded configuration, as shown in FIG. 9, by injection of inflation fluid, such as dilute radiopaque contrast, into proximal inflation port 614 (shown in FIG. 7), through first lumen 618, and into occluder 610.

Figure 10:
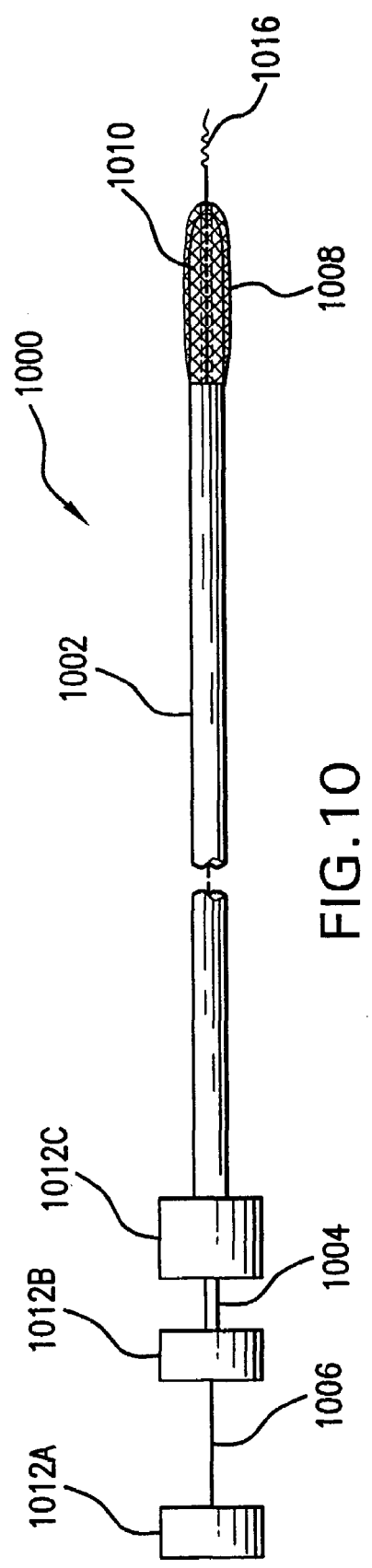
FIG. 10 illustrates a side view of a third embodiment of a distal protection system according to the present invention.

FIG. 10 illustrates a third embodiment of the invention. A distal protection device 1000 includes an inner wire 1006, which is slidably disposed within a hollow push rod 1004 and is similar to inner wire 106, described above. A distal flexible tip 1016, similar to distal flexible tip 116, may also be included. Hollow push rod 1004 is slidably disposed within an outer tube 1002. Distal protection system 1000 may also be termed a "fixed-wire" embodiment because inner wire 1006 is slidable within, but not removable from, hollow push rod 1004. In distal protection system 1000, an occluder 1010 is not inflated hydraulically, as described above regarding occluders 110, 610. Rather, occluder 1010 is mechanically expandable, thus eliminating fittings 113, 613 and any inflation accessories that would otherwise be required.

Both hollow push rod 1004 and outer tube 1002 are similar in materials, dimensions and construction to hollow push rod 104, described above. Because both filter 1008 and occluder 1010 are deployed by push-pull mechanisms, as will be described below, the staggered proximal ends of inner wire 1006, hollow push rod 1004, and outer tube 1002 may be conveniently fitted with handles 1012A, 1012B, and 1012C, respectively.

Figure 11:
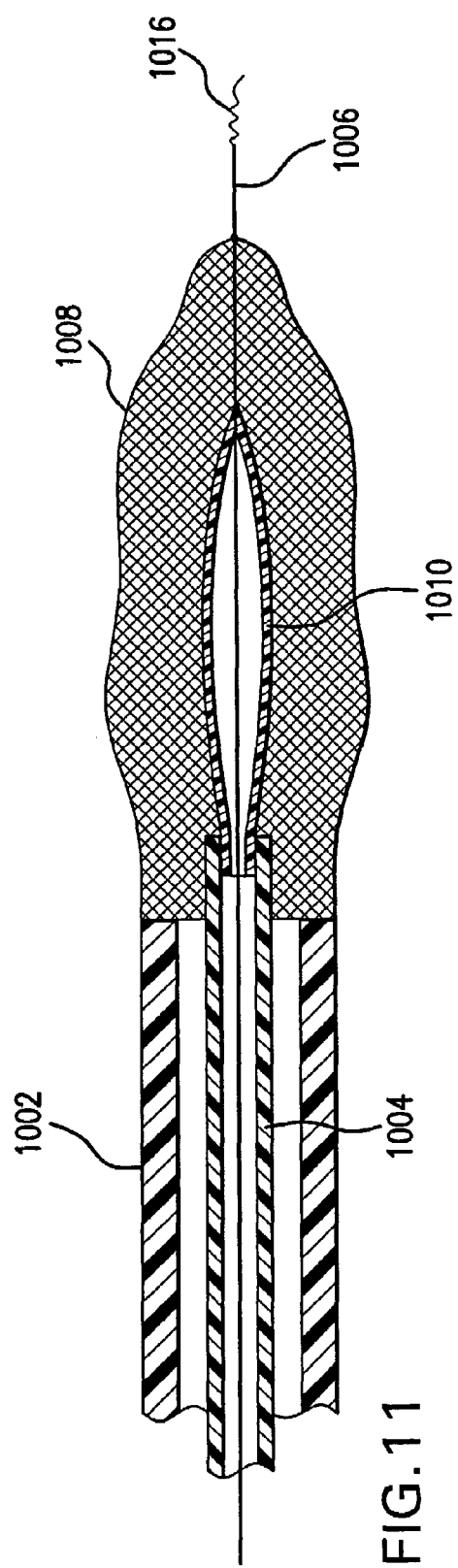
FIG. 11 illustrates a longitudinal cross-sectional view of a distal end of the distal protection system of FIG. 10, shown in a fully collapsed configuration.

As is shown in FIG. 11, filter 1008 and occluder 1010 are disposed on a distal region of distal protection system 1000. Filter 1008 is similar to filter 108, described above; in that filter 1008 may be any filter known in the art. A proximal end of filter 1008 is fixedly attached to a distal end of outer tube 1002. A distal end of filter 1008 is fixedly attached to inner wire 1006 adjacent flexible tip 1016. Filter 1008 may be expanded from the collapsed configuration shown in FIG. 11 to the expanded or deployed configuration shown in FIG. 12 by pushing outer tube 1002 distally while holding inner wire 1006 steady. This manipulation can be performed at the proximal end of the device by advancing handle 1012C while holding handle 1012A in a fixed position with respect to the patient. Reversing this manipulation will return filter 1008 to the collapsed configuration shown in FIG. 11.

Occluder 1010 is not an inflatable occluder like occluder 110, described above. Rather, occluder 1010 is a mechanically expandable occlusion device. Such devices are known in the art, and one example thereof comprises a series of flexible support ribs or struts having a non-porous material stretched there over. Appropriate materials for the ribs include stainless steel, nitinol, other biocompatible metals and polymers having a suitably high Young's modulus. The non-porous occluder-covering material may be a thin, biocompatible, elastic film made of a material selected from those listed above for use in the inflatable occluders 110, 610. Other flexible non-porous materials that will cling to the support struts may also be suitable as an occluder-covering material.

A proximal end of occluder 1010 is fixedly attached to a distal end of hollow push rod 1004. A distal end of occluder 1010 is fixedly attached to inner wire 1006 at a location proximal to, or within, the attachment joint of the distal end of filter 1008. As with the other embodiments described above, occluder 1010 is contained within filter 1008 to provide a nested arrangement that is axially compact and minimizes the overall length of the combined distal protection elements.

Although filter 1008 and occluder 1010 are nested, each of these expandable protection elements has a separate deployment mechanism. For example, if filter 1008 has already been deployed, then occluder 1010 may be deployed into the expanded configuration shown in FIG. 13 by pushing hollow push rod 1004 distally while holding inner wire 1006 and outer tube 1002 steady. This manipulation can be performed at the proximal end of distal protection system 1000 by advancing handle 1012B while holding handles 1012A and 1012C in fixed positions with respect to the patient. Managing the positions of all three handles may be simplified by use of an accessory body (not shown) that can hold handles 1012A, 1012B, and 1012C in position unless the clinician moves them.

Figure 13:
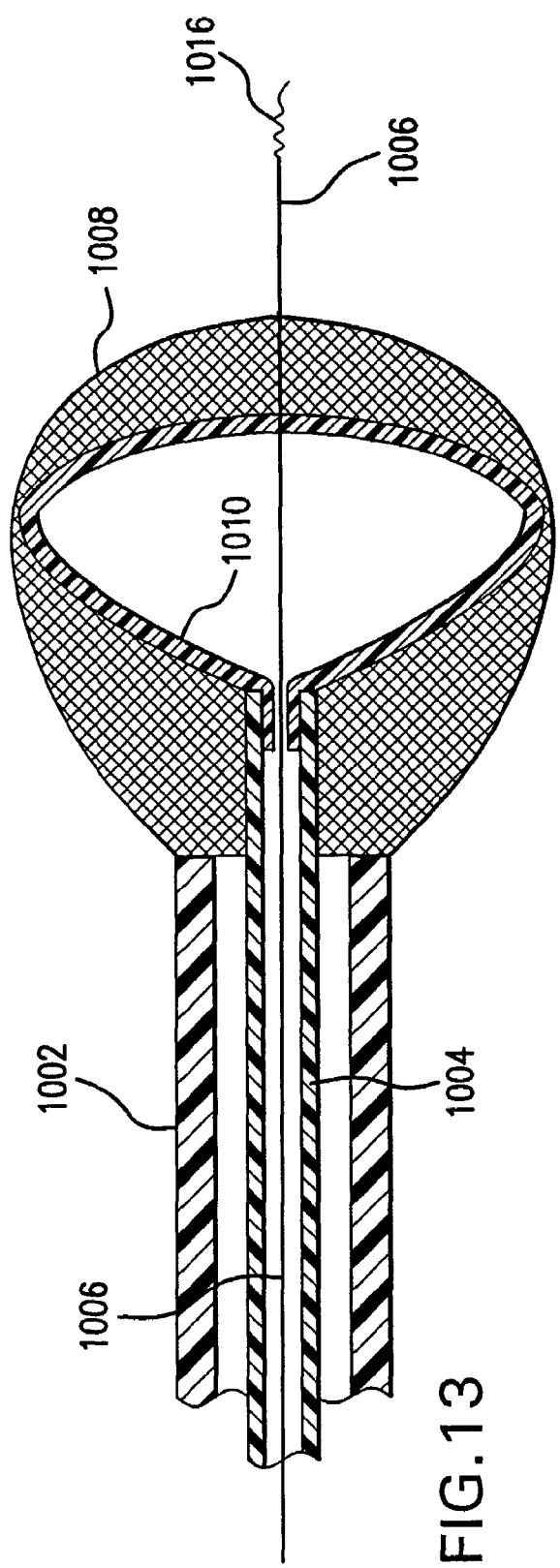
FIG. 13 illustrates a longitudinal cross-sectional view of the distal end of the distal protection system of FIG. 10, shown with both the filter and the occluder expanded.

If filter 1008 has not been deployed already, then filter 1008 and occluder 1010 may be deployed simultaneously into the expanded configuration shown in FIG. 13 by pushing hollow push rod 1004 and outer tube 1002 distally at the same time, while holding inner wire 1006 steady. Alternatively, hollow push rod 1004 may be actuated alone, while outer tube 1002 is allowed to slide freely so that filter 1008 is driven open by the expanding movement of occluder 1010 there within.

Figure 12:
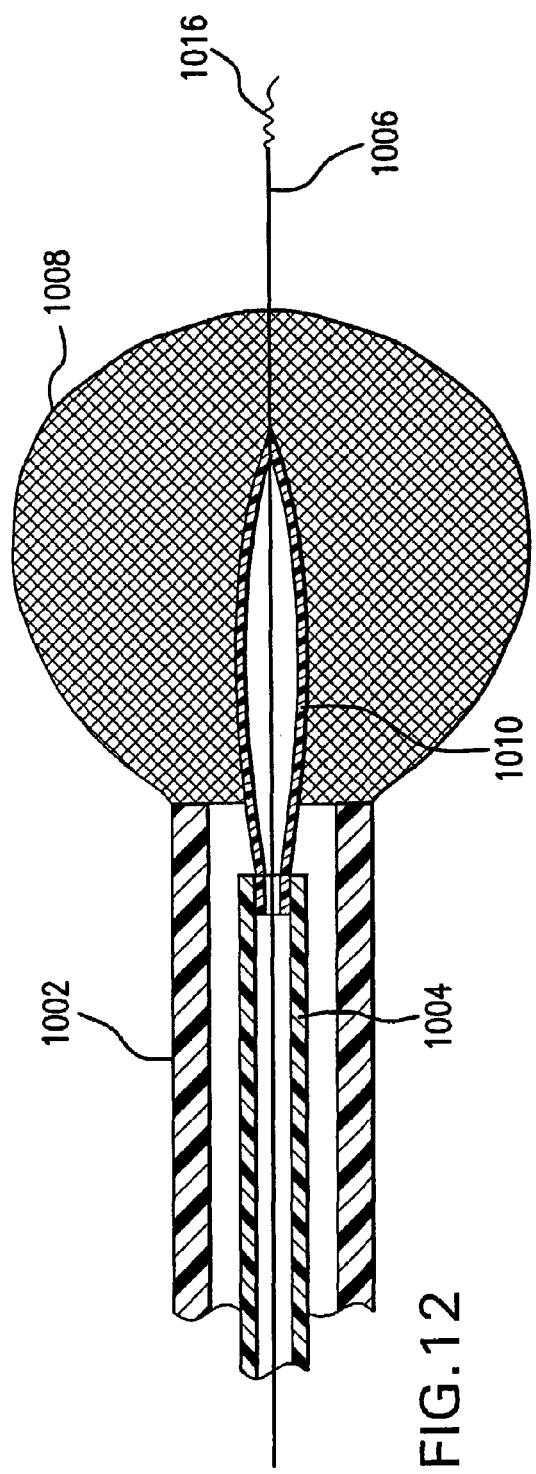
FIG. 12 illustrates a longitudinal cross-sectional view of the distal end of the distal protection system of FIG. 10, shown with the filter expanded.

After both expandable elements have been deployed, pulling inner tube 1004 proximally and/or pushing inner wire 1006 distally will return occluder 1010 to the collapsed configuration shown in FIGS. 11 and 12, while filter 1008 remains expanded. Filter 1008 and occluder 1010 can also be collapsed together by simultaneously operating both deployment mechanisms. Alternatively, filter 1008 and occluder 1010 can be collapsed concurrently by manipulating outer tube 1002 with respect to inner wire 1006 while hollow push rod 1004 is allowed to slide freely so that occluder 1010 is forced closed by the collapsing movement of filter 1008.

Figure 14:
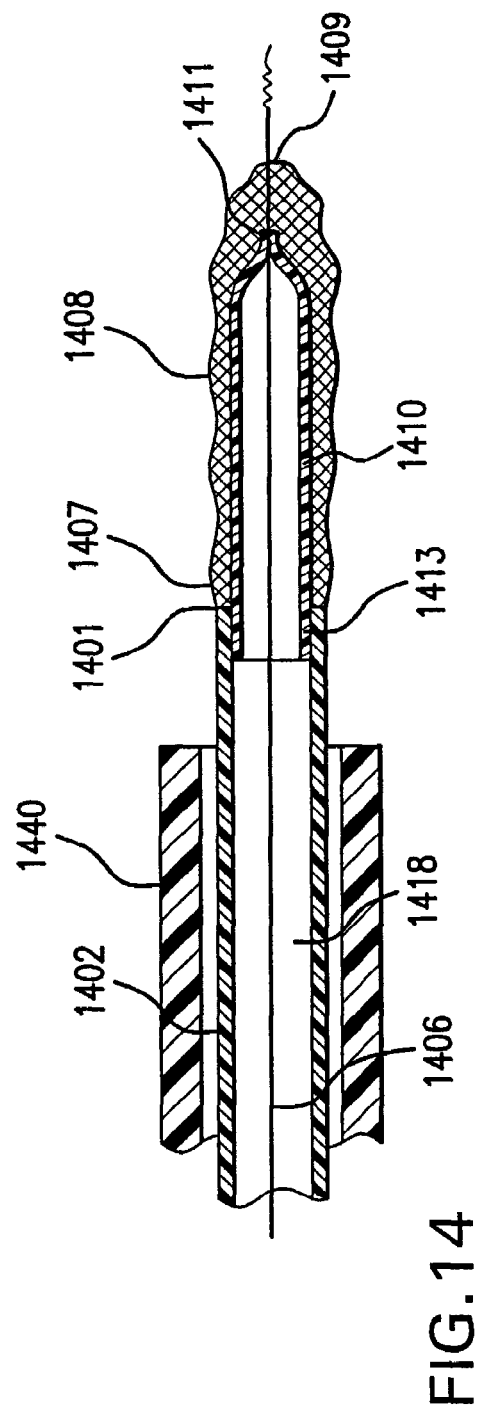
FIG. 14 illustrates a longitudinal cross-sectional view of a distal end of a fourth embodiment of the distal protection system according to the present invention, shown with both the filter and the occluder in a fully collapsed configuration.

Referring now to FIG. 14, a fourth embodiment of the present invention is illustrated. In this embodiment, a tube 1402 has an inflation lumen 1418 extending therethrough. Tube 1402 is similar in materials, dimensions and construction to hollow push rod 104, described above.

An inner wire 1406, similar to inner wire 106, described above, is disposed within inflation lumen 1418. However, in this embodiment, inner wire 1406 is not slidable with respect to tube 1402.

A filter 1408 is also provided in this embodiment. Filter 1408 serves the same function as filter 108, described above. Also similar to filter 108, filter 1408 is a porous material made of braided or woven filaments. However, filter 1408 is made from a more ductile, inelastic material than filter 108, similar to materials used in the art for the construction of stents. Appropriate materials include stainless steel, nitinol, and cobalt-type alloys such as 316L and ELGILOY®. A filter proximal end 1407 is fixedly attached to a tube distal end 1401. A filter distal end 1409 is fixedly attached to inner wire 1406.

An occluder 1410 is nested within and surrounded by filter 1408. Occluder 1410 is similar in dimension and materials to inflatable occluder 110, described above. An occluder proximal end 1413 is sealingly attached to tube 1402 so that occluder 1410 is in fluid communication with inflation lumen 1418. An occluder distal end 1411 is sealingly attached to inner wire 1406 proximal to filter distal end 1409.

Figure 15:
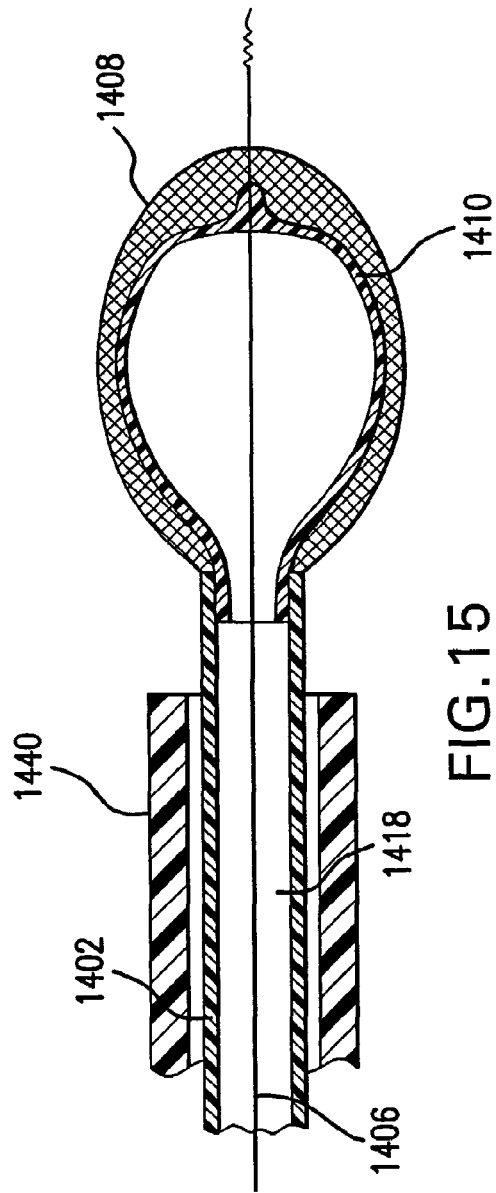
FIG. 15 illustrates a longitudinal cross-sectional view of the distal end of the distal protection system of FIG. 14, shown with both the filter and the occluder expanded.

Filter 1408 and occluder 1410 are introduced into a patient's body lumen and positioned downstream of the treatment area in a collapsed configuration, as shown in FIG. 14. When distal protection is needed during a procedure, occluder 1410 is inflated, in a manner similar to the inflation of occluder 110, described above. However, the inflation of occluder 1410 also causes filter 1408 to expand. This configuration is shown in FIG. 15. In other words, unlike the previous embodiments described above, filter 1408 is not separately expandable from occluder 1410, such as with a separate push-pull mechanism as described above.

Figure 16:
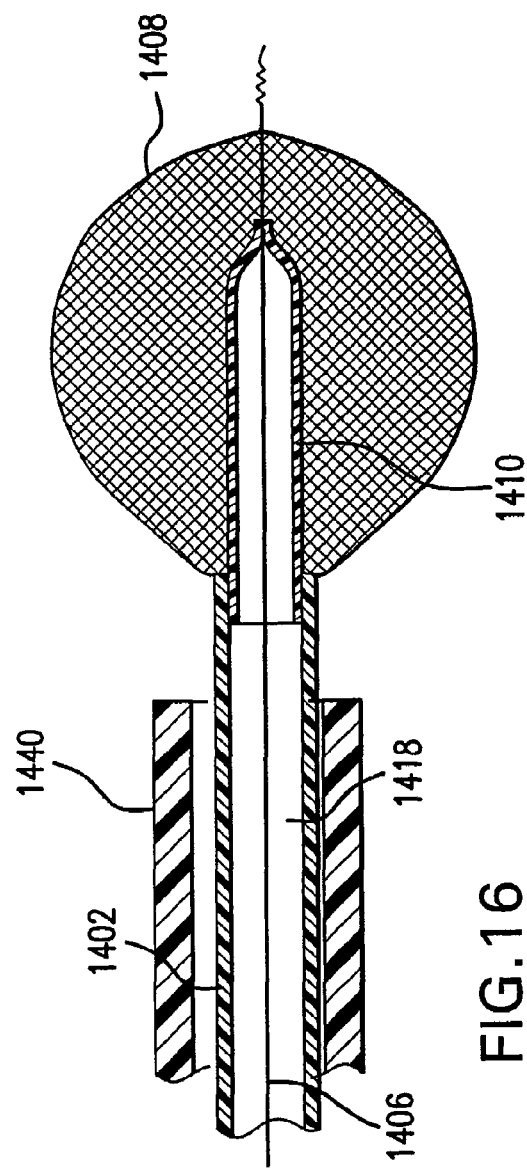
FIG. 16 illustrates a longitudinal cross-sectional view of the distal end of the distal protection system of FIG. 14, shown with the filter expanded and the occluder collapsed.

As shown in FIG. 16, when occlusion of a vessel is no longer desirable, occluder 1410 is deflated. Because filter 1408 is constructed from an inelastic material, filter 1408 remains expanded even after occluder 1410 is deflated. Filter 1408 can thus remain in the deployed configuration for the duration of the procedure, while occluder 1410 is inflated and deflated as needed.

Figure 17:
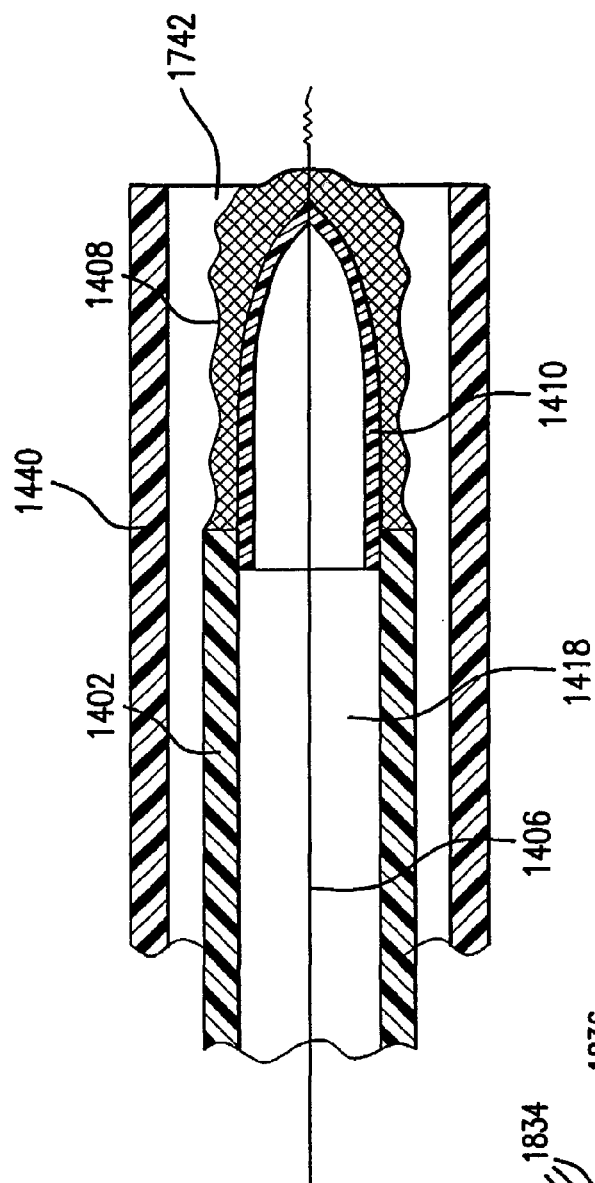
FIG. 17 illustrates a longitudinal cross-sectional view of the distal end of the distal protection system of FIG. 14, shown with the filter re-collapsed by an outer sheath.

In order to withdraw filter 1408 from the patient, filter 1408 must be collapsed to the configuration shown in FIG. 17. As this embodiment does not utilize the push-pull configuration of the embodiments described above, a sheath catheter 1740 must be passed over tube 1402 and filter 1408 to force filter 1408 to resume a low profile. Sheath 1740 includes a lumen 1742 sized so that tube 1402 may be nested therewithin. Sheath 1740 is otherwise similar in materials and length to tube 1402, although sheath 1740 may be slightly longer than tube 1402 to facilitate the capture of filter 1408.

In addition to collapsing filter 1408 for withdrawal, sheath 1740 also smooths the outer profile of filter 1408. The smoother profile may assist in moving filter 1408 past the treatment area, especially if a stent or other device has been deployed, as unsheathed filter 1408 may catch upon such devices.

Figure 18:
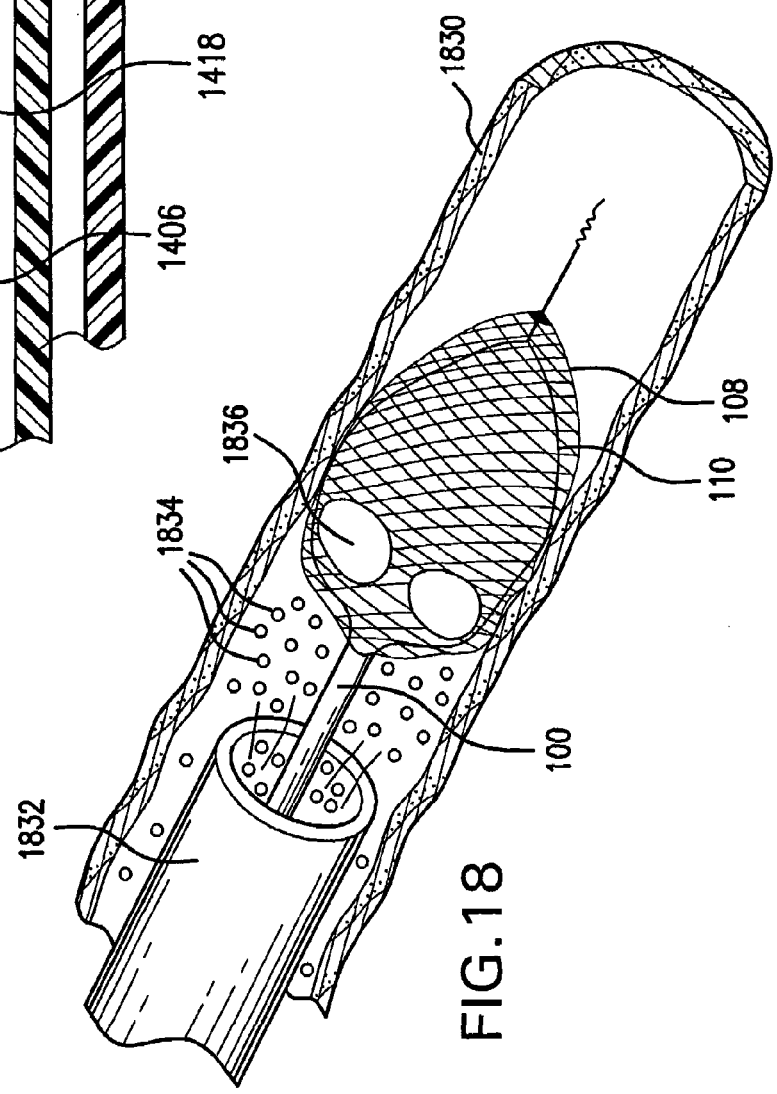
FIG. 18 is a cut-away perspective view of the distal protection system of FIG. 1 with an aspiration catheter, shown with both the occluder and the filter expanded in a body lumen.

FIGS. 18, 19, and 20 illustrate the use of distal protection system 100, although the procedure shown and described herein is equally applicable to all embodiments of the present invention. FIG. 18 shows distal protection system 100 within vessel 1830. Filter 108 and occluder 110 have been positioned downstream of a treatment area (not shown), and both filter 108 and occluder 110 have been expanded or deployed according to the procedures described above. A therapeutic catheter (not shown) has been inserted into vessel 1830 to perform a procedure, such as a PTCA, at the treatment area. Preferably, filter 108 and/or occluder 110 were deployed prior to the (PTCA) procedure.

While performing the procedure, embolic particles 1834 have been released into the blood stream. Occluder 110 completely blocks vessel 1830 so that embolic particles 1834 cannot travel further downstream. Aspiration catheter 1832 is introduced into vessel 1830, as by introduction alongside (not shown) or over distal protection system 100. Aspiration catheter 1832 is then used to evacuate as many embolic particles 1834 as possible, in accordance with occlusion/aspiration methods known in the art. Alternatively, trapped embolic particles 1834 may be lysed (disintegrated into the blood stream, such as with a laser, thrombolytic agent or chemical solvent), or left intact for subsequent capture within filter 108.

FIG. 19 shows vessel 1830 after aspiration catheter 1832 has been removed. Occluder 110 has been deflated or collapsed according to the procedures described above, but filter 108 remains deployed, in apposition with the wall of vessel 1830. Blood flow has resumed, and any remaining embolic particles 1834 are carried into filter 108 through inlets 1836. Embolic particles 1834 are then filtered from the bloodstream and remain within filter 108.

FIG. 20 shows vessel 1830 after filter 108 has also been collapsed according to the procedures described above. Embolic particles 1834 are trapped within filter 108 and can be withdrawn from vessel 1830 along with the withdrawal of distal protection system 100.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A distal protection device for use with a catheter during a vascular procedure comprising:

a tube having a proximal end and a distal end and a tube lumen extending there through;

an elongate wire extending through the tube lumen;

an expandable filter having proximal and distal ends, wherein at least one of the filter ends is fixedly attached to at least one of the distal end of the tube or the wire;

an expandable occluder having a proximal end and a distal end positioned within the filter;

a hollow push rod having proximal and distal ends and a rod lumen extending there through, the push rod being slidably disposed within the tube lumen and extending distally and proximally there from; and wherein the elongate wire slidably extends through the rod lumen, the filter proximal end is fixedly attached to the tube distal end, the filter distal end is fixedly attached to the push rod distal end, the occluder distal end is sealingly attached adjacent the push rod distal end, and the occluder proximal end is sealingly attached to the tube distal end such that an interior of the occluder is in fluid communication with the tube lumen.

2. The distal protection device according to claim 1, wherein the occluder is a balloon.

3. The distal protection device according to claim 1, wherein the wire includes a flexible distal tip.

4. The distal protection device according to claim 1, wherein an inflation port is disposed adjacent a device proximal end and is in fluid communication with the tube lumen.

5. The distal protection device according to claim 1, wherein the push rod proximal end is attached to a handle.

6. The distal protection device according to claim 1, wherein a proximal end of the push rod is attached to a handle.

7. A distal protection device comprising:

a tube having a proximal end and a distal end and a tube lumen extending there through;

a hollow push rod having proximal and distal ends and a rod lumen extending there through, the push rod being slidably disposed within the tube lumen and extending distally and proximally there from;

an expandable filter having a filter proximal end fixedly attached to the tube distal end and a filter distal end fixedly attached to the rod distal end; and an expandable occluder disposed within the filter and having an occluder distal end sealingly attached adjacent the push rod distal end and an occluder proximal end sealingly attached to the tube distal end such that an interior of the occluder is in fluid communication with the tube lumen.

8. A distal protection device comprising:

an elongate tube having proximal and distal ends and a tube lumen extending there through;

an expandable filter extending distally beyond the tube and having a filter proximal end fixedly attached to the tube distal end; and an expandable occluder disposed within the filter and having an occluder proximal end sealingly attached to the tube distal end such that an interior of the occluder is in fluid communication with the tube lumen.

9. The distal protection device of claim 8 further comprising a hollow push rod having proximal and distal ends and a rod lumen extending there through, the push rod being slidably disposed within the tube lumen and extending distally and proximally there from, a filter distal end being fixedly attached to the rod distal end, and an occluder distal end being sealingly attached adjacent the push rod distal end.

10. The distal protection device of claim 9 further comprising an elongate wire slidably disposed within and removable from the rod lumen.

\* \* \* \* \*